United States Patent [19]

Hasegawa et al.

[11] Patent Number: 5,689,001
[45] Date of Patent: Nov. 18, 1997

[54] PROCESS FOR PURIFYING VALINE

[75] Inventors: Kazuhiro Hasegawa; Tetsuya Kaneko; Noriko Takahashi; Chiaki Sano, all of Kawasaki, Japan

[73] Assignee: Ajinomoto Co., Inc., Tokyo, Japan

[21] Appl. No.: 661,117

[22] Filed: Jun. 10, 1996

[30]  Foreign Application Priority Data

Jun. 12, 1995  [JP]  Japan ................................ 7-144843

[51]  Int. Cl.$^6$ ................................................ C07C 227/00
[52]  U.S. Cl. ................................ 562/554; 562/85
[58]  Field of Search ................................ 562/85, 554

[56]  References Cited

U.S. PATENT DOCUMENTS 2,894,954  7/1959  Dewutt ................................ 562/554

FOREIGN PATENT DOCUMENTS

| 40-11373 | 6/1965 | Japan . |
| 45-1055  | 1/1970 | Japan . |
| 52-3016  | 1/1977 | Japan . |

OTHER PUBLICATIONS

Doherty, J. Biol. Chem., vol. 135, pp.487–496, 1940.

*Primary Examiner*—Michael L. Shippen
*Attorney, Agent, or Firm*—Oblon, Spivak, McClelland, Maier & Neustadt, P.C.

[57]  ABSTRACT

A process is provided for obtaining high-purity valine in high yield by a simple method using an inexpensive precipitant of p-isopropylbenzene sulfonic acid or a water-soluble salt thereof.

20 Claims, 2 Drawing Sheets

PROCESS FOR PURIFYING VALINE

BACKGROUND OF THE INVENTION

1. Field of the Invention

The present invention relates to a novel valine isopropylbenzenesulfonate crystal which is suitable for the purification of valine and a process for purifying valine using the valine isopropylbenzenesulfonate.

2. Discussion of the Background

L-valine is useful as a starting material for medical amino acid preparations and as a synthetic intermediate of various medications. Further, L-valine is useful as an intermediate of agricultural chemicals.

Valine is generally produced by hydrolysis of proteins, such as soybean protein, or by fermentation of microorganisms having the ability to produce valine. Conventional methods of separating valine from the resulting valine-containing aqueous solutions, such as protein hydrolyzates or fermentation solutions, and purifying the same include the following:

(1) a method involving separation and removal of acidic and basic amino acids through treatment using an ion-exchange resin, leaving a neutral amino acid fraction. This is repeatedly recrystallized to remove the neutral amino acids other than valine [Biochem. J., 48, 313 (1951)].

(2) a method in which hydrochloric acid is added to a valine-containing aqueous solution to form and precipitate valine hydrochloride crystals, and this procedure is repeated [Japanese Laid-Open Patent Application (Kokai) No. 16,450/1981].

However, these methods have problems. Method (1) is quite intricate and the separation of valine from leucine and isoleucine is very difficult. In method (2), the solubility of valine hydrochloride crystals in water is so high that the yield of valine is decreased.

In a further purification method, valine is purified by reacting it with a precipitant such as tetrachloroorthophthalic acid, sulfoisophthalic acid, or flavianic acid, which selectively forms an adduct with valine (Japanese Patent Publication No. 25,059/1967). However, this method has suffered the problems that (a) the precipitant used is expensive and industrially hard to obtain, (b) since the solubility of the resulting adduct is high, it is difficult to recover valine in high yield, and (c) isolation of valine from the adduct is complicated.

Further, as a precipitant of leucine (which is a neutral amino acid having a structure similar to valine), 1,2-dimethylbenzenesulfonic acid (Japanese Patent Publication No. 11,373/1965) and p-toluenesulfonic acid [Japanese Laid-open Patent Application (Kokai) No. 3,016/1977] are known. However, since these precipitants are specific to leucine, they do not work well at all as precipitants of valine. Thus, the precipitants are specific substances, and it has not been easy to find a precipitant specific to valine.

SUMMARY OF THE INVENTION

Accordingly, one object of the present invention is to provide a simple process for purifying valine having a high purity in high yield using an inexpensive precipitant.

A further object of the present invention is to provide an inexpensive precipitant specific for the precipitation of valine.

These and other objects of the present invention have been satisfied by the discovery that when a valine-containing aqueous solution is reacted with p-isopropylbenzenesulfonic acid and then cooled, valine p-isopropylbenzenesulfonate crystals, which are sparingly-soluble salts, are precipitated selectively.

BRIEF DESCRIPTION OF THE FIGURES

A more complete appreciation of the invention and many of the attendant advantages thereof will be readily obtained as the same becomes better understood by reference to the following detailed description when considered in connection with the accompanying figures, wherein.

DETAILED DESCRIPTION OF THE PREFERRED EMBODIMENTS

Figure 1:
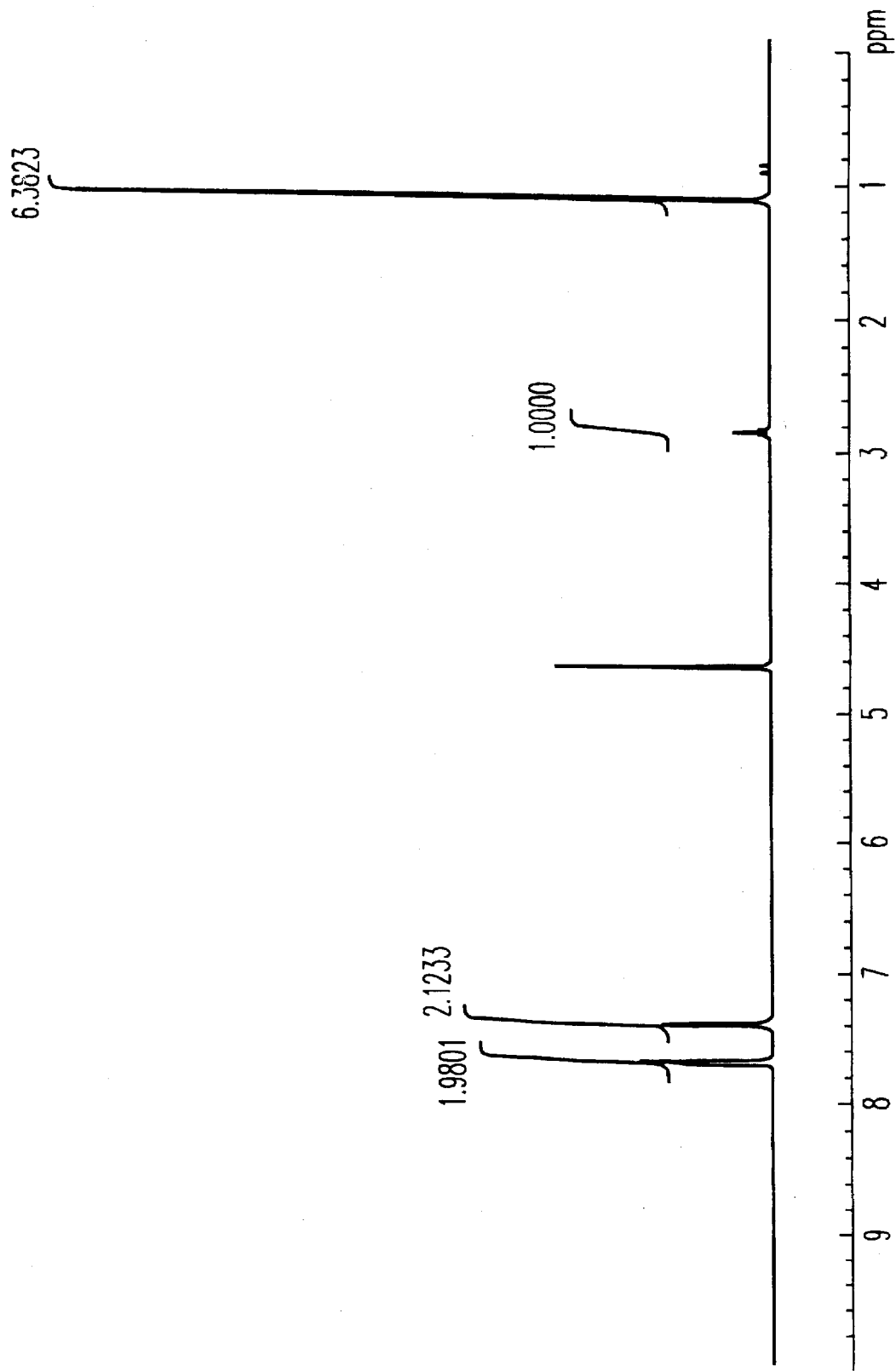
FIG. 1 shows a $^1$H-NMR spectrum of sodium isopropylbenzenesulfonate obtained in Reference Example 1.

The present invention relates to:

(1) a valine p-isopropylbenzenesulfonate crystal comprising 1 mol of valine and 1 mol of p-isopropylbenzenesulfonic acid, and (2) a process for purifying valine, which comprises contacting a valine-containing aqueous solution with p-isopropylbenzenesulfonic acid or its water-soluble salt to form a valine p-isopropylbenzenesulfonate crystal, separating the valine p-isopropylbenzenesulfonate from the rest of the solution, and dissociating the valine p-isopropylbenzenesulfonate to obtain valine.

The valine used in the process of the present invention, can be optically active (i.e. an L-isomer or a D-isomer), a racemic modification or a mixture thereof. Any valine-containing aqueous solution is suitable for use in the present process. Examples of the valine-containing aqueous solutions of the present invention include an mixed amino acid solution obtained by separating and removing basic amino acids from a hydrolyzate formed by hydrolyzing proteins, such as soybean protein, a fermentation solution obtained by incubating microorganisms having the ability to form and accumulate valine, a solution obtained by removing cells from this fermentation solution, a solution obtained by treating the above-mentioned solution through an ion-exchange resin or an adsorption resin, and an aqueous solution of crude DL-valine obtained synthetically in which hydantoin derivatives are formed during the reaction.

The p-isopropylbenzenesulfonic acid used in the present invention can be easily formed by sulfonation of isopropylbenzene. As an example, isopropylbenzene and conc. sulfuric acid in an amount of 1.5 mols, per mol of isopropylbenzene, can be charged into a glass container, and the mixture heated at 120° C. for from 2 to 3 hours. This provides a ready preparation of the p-isopropylbenzenesulfonic acid that is low in cost and industrially useful. The p-isopropylbenzenesulfonic acid may be used in the form of its free acid, or its water-soluble salt. Suitable examples of water soluble salts include alkali metal salts such as the sodium salt or potassium salt, alkaline-earth metal salts such as the calcium salts, or an ammonium salt. p-Isopropylbenzenesulfonic acid or its water-soluble salt is used in an amount which is equimolar to or more than the amount of valine contained in the aqueous solution, preferably from 1.0 to 1.1 mols per mol of valine. While it is possible to perform the present invention using excess p-isopropylbenzenesulfonic acid or its salt, there is no need to use a large excess in order to obtain high efficiency in the removal of valine from the aqueous solution.

The valine p-isopropylbenzenesulfonate crystals are only sparingly soluble in water. This addition compound can be formed and precipitated by adding p-isopropylbenzenesulfonic acid or its water-soluble salt to an aqueous solution containing 3 g/dl or more of valine and adjusting the pH to approximately 1.5. The pH of the solution suitable for formation and precipitation of the valine p-isopropylbenzenesulfonate crystal is between 0.1 and 2.3, more preferably between 1.0 and 1.7. While any acid that does not disrupt the valine p-isopropylbenzenesulfonate crystal can be used for the precipitation, preferred acids for adjusting the pH include inorganic acids such as hydrochloric acid and sulfuric acid. When a seed crystal of valine p-isopropylbenzenesulfonate is added to a mixed solution of valine p-isopropylbenzenesulfonate and p-isopropylbenzenesulfonic acid as required, the valine containing crystals can be precipitated efficiently. When the valine aqueous solution is dilute, the valine p-isopropylbenzenesulfonate crystal can be precipitated through concentration. In this case, p-isopropylbenzenesulfonic acid may be added at any stage before or after the concentration step. When the valine aqueous solution is concentrated under neutral conditions, the crystals of the free valine are precipitated. The valine isopropylbenzenesulfonate crystals can be easily formed by adding thereto an appropriate amount of p-isopropylbenzenesulfonic acid as such and adjusting the pH to approximately 1.5. Further, the valine p-isopropylbenzenesulfonate crystals can also be precipitated through concentration by adjusting the pH of a valine dilute solution containing an appropriate amount of p-isopropylbenzenesulfonic acid to approximately 2 in advance, and then concentrating the solution.

The precipitated valine p-isopropylbenzenesulfonate crystals may be separated by conventional solid-liquid separation methods such as filtration or centrifugation. Although the separated crystals have high purity, they can be further purified by a conventional purification method such as washing, dehydration, or recrystallization.

The thus-obtained crystalline valine p-isopropylbenzenesulfonate comprising 1 mol of valine and 1 mol of p-isopropylbenzenesulfonic acid is a novel product which exhibits the following properties:

White plate crystal. Soluble in water and ethanol.
Solubility in water: 7.8% by weight (pH 1.5, 10° C.)
Crystal structure: monoclinic system
Crystal density: 1.28/cm$^3$
Elemental analysis: found: C 52.9%, H 7.3%, N 4.4%, S 9.9% calculated: C 53.0%, H 7.3%, N 4.4%, S 10.1%

In order to isolate free valine from the valine p-isopropylbenzenesulfonate crystal, the solution containing a large amount of hot water is brought into contact with a weakly basic ion-exchange resin (OH-type), or an alkali such as sodium hydroxide is added thereto. When using the ion-exchange resin, p-isopropylbenzenesulfonic acid is adsorbed onto the resin and the free valine is obtained in the effluent. This solution is treated in a conventional manner, such as crystallization through concentration, to obtain the valine crystals. The precipitant (p-isopropylbenzenesulfonic acid) adsorbed on the resin is then eluted as an alkali salt when the resin is regenerated with an alkaline solution, such as a sodium hydroxide solution.

When the alkali addition method is used, the alkali, such as sodium hydroxide, is added to an aqueous suspension of the crystalline valine p-isopropylbenzenesulfonate either as such or in the form of an aqueous solution to adjust the pH to between 5 and 8, preferably between 6 and 7, whereby p-isopropylbenzenesulfonic acid is dissolved in the solution as an alkali salt, the free valine is precipitated, and the precipitated valine is obtained through separation.

The precipitant (p-isopropylbenzenesulfonic acid) which has been separated and recovered as the alkali salt can be reused, as such, as a precipitant in the subsequent reaction.

Having generally described this invention, a further understanding can be obtained by reference to certain specific examples which are provided herein for purposes of illustration only and are not intended to be limiting unless otherwise specified.

EXAMPLES

The amounts of valine and other amino acids in the following Examples were determined using a Hitachi L-8500 Model amino acid analyzer.

Reference Example 1

(Production of p-isopropylbenzenesulfonic acid)

Conc. sulfuric acid (84 ml, 1.5 mols) was added to 140 ml (1 mol) of isopropylbenzene, and the mixture was stirred at a temperature of from 120° to 130° C. for 2.5 hours. If unreacted isopropylbenzene remains, layer separation is observed. The reaction was deemed completed when no layer separation was observed, and a solution containing p-isopropylbenzenesulfonic acid as the main ingredient was obtained. This solution was charged into 350 ml of water, and partially neutralized with sodium hydrogencarbonate. The p-isopropylbenzenesulfonic acid was then converted into a sodium salt with sodium hydroxide to precipitate a sodium p-isopropylbenzenesulfonate crystal. The thus-obtained crystal was separated through filtration, and then dried under reduced pressure. This sodium p-isopropylbenzenesulfonate was easily soluble in water and slightly soluble in ethanol. The $^1$H-NMR spectrum of the thus-obtained crystal is shown in FIG. 1.

Example 1

Figure 2:
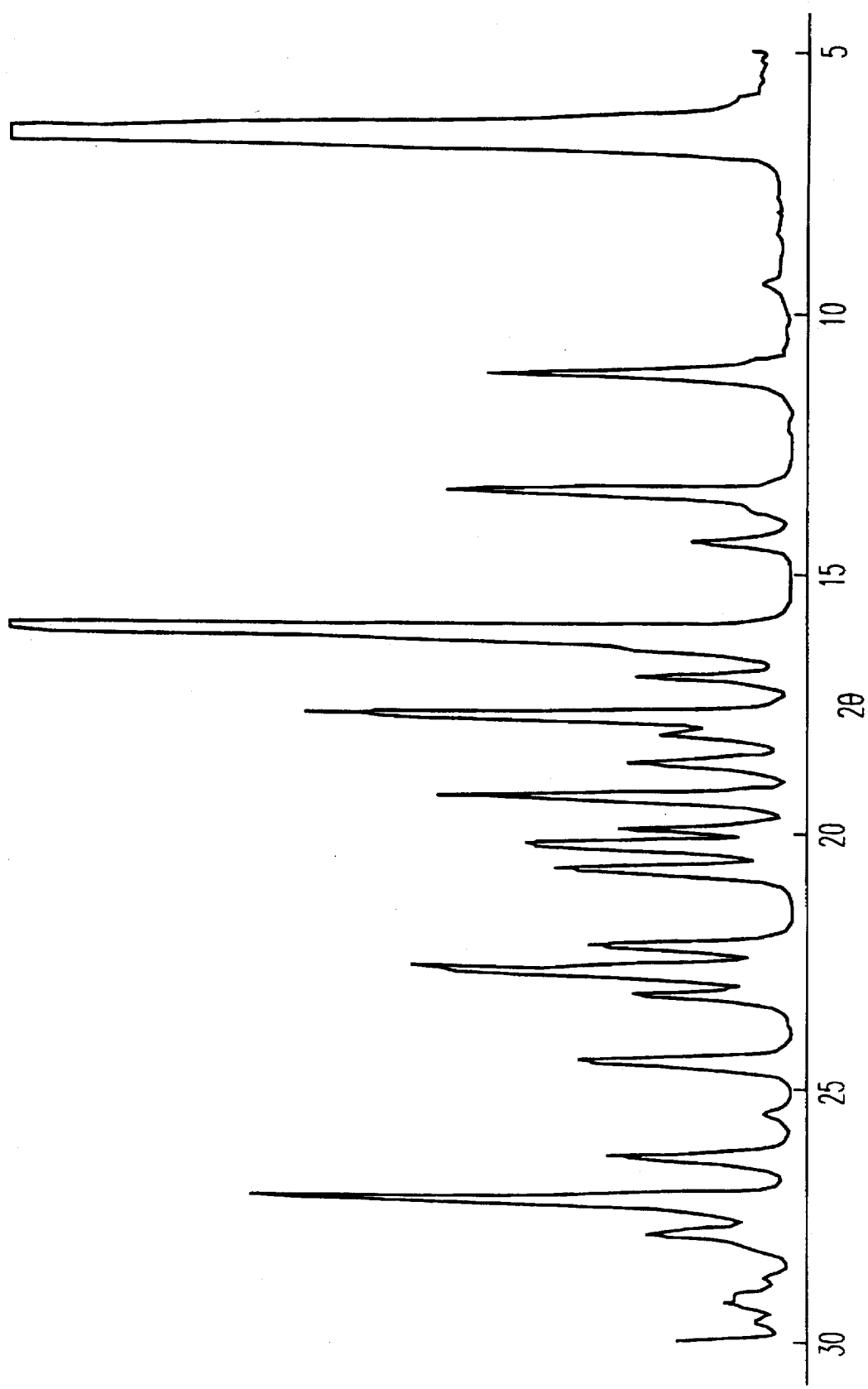
FIG. 2 is a powder X-ray diffraction pattern of L-valine p-isopropylbenzenesulfonate obtained in Example 1.

Seventy milliliters of water were added to 10 g of L-valine and 19 g of sodium p-isopropylbenzenesulfonate obtained in Reference Example 1, and the pH of the solution was adjusted to 1.5 with sulfuric acid. The temperature of the solution was then raised to 50° C. to dissolve the solid therein. Subsequently, the solution was cooled to 10° C. to precipitate crystalline L-valine p-isopropylbenzenesulfonate. The precipitated crystals were separated through filtration, and dried under reduced pressure. The thus-obtained L-valine p-isopropylbenzenesulfonate was white fine crystals. The crystal system thereof was monoclinic, and the specific gravity of the crystals was 1.28 g/cm$^3$. The powder X-ray diffraction pattern of the crystals is shown in FIG. 2. The X-ray diffraction was conducted using Cu-Kα rays as a radiation source. The elemental analysis of the crystals revealed the following composition.

C 53.1%, H 7.2%, N 4.4%, S 10.0%

Example 2

Sodium p-isopropylbenzenesulfonate (26.6 g, equimolar amount relative to valine) was added to 100 ml of a solution containing 14 g of L-valine, 1.1 g of L-leucine, 1.1 g of L-isoleucine, 1.1 g of L-glutamic acid and 1.1 g of L-alanine and the pH of the solution was adjusted to 1.5 with sulfuric acid. Then, the mixture was dissolved under heat.

Subsequently, the solution was cooled to precipitate crystalline L-valine p-isopropylbenzenesulfonate. The precipitated crystals were recovered by centrifugation, and then dissolved in a large amount of hot water. The solution was passed through an OH-type weakly basic ion-exchange resin to remove p-isopropylbenzenesulfonic acid. The effluent was crystallized through concentration to obtain 9 g of free L-valine crystals. The analysis of the mother liquor revealed that the precipitation rate of valine was 70% and the purity of the free L-valine was 97%. The contents of the other amino acids were 3% or less.

Example 3

Sodium p-isopropylbenzenesulfonate (26.6 g, equimolar amount relative to valine) was added to 100 ml of a solution containing 14 g of L-valine, 0.42 g of L-leucine, 0.42 g of L-isoleucine, 0.42 g of L-glutamic acid and 0.42 g of L-alanine and the pH of the solution was adjusted to 1.5 with sulfuric acid. Then, the mixture was dissolved under heat. Subsequently, the solution was cooled to precipitate crystalline L-valine p-isopropylbenzenesulfonate. The precipitated crystals were recovered by centrifugation, and then dissolved in a large amount of hot water. The solution was passed through an OH-type weakly basic ion-exchange resin to remove p-isopropylbenzenesulfonic acid. The effluent was crystallized through concentration to obtain 9 g of free L-valine crystals. The analysis of the mother liquor revealed that the precipitation rate of valine was 70% and the purity of the free L-valine was 99%. The contents of the other amino acids were 1% or less.

Example 4

Sodium p-isopropylbenzenesulfonate (19 g, equimolar amount relative to valine) was added to 100 ml of a solution containing 10 g of D-valine, 0.3 g of D-leucine and 0.3 g of D-isoleucine and the pH of the solution was adjusted to 1.5 with sulfuric acid. Then, the mixture was dissolved under heat. Subsequently, the solution was cooled to precipitate 18 g of crystalline D-valine p-isopropylbenzenesulfonate. The precipitated crystals were recovered by centrifugation, and then dissolved in a large amount of hot water. The solution was passed through an OH-type weakly basic ion-exchange resin to remove p-isopropylbenzenesulfonic acid. The effluent was crystallized through concentration to obtain 6.5 g of free D-valine crystals. The analysis of the mother liquor revealed that the precipitation rate of valine was 70% and the purity of the free D-valine was 99%. The contents of the other amino acids were 1% or less.

Example 5

Sodium p-isopropylbenzenesulfonate (19 g, equimolar amount relative to valine) was added to 100 ml of a solution containing 10 g of DL-valine, 0.3 g of L-leucine and 0.3 g of L-isoleucine and the pH of the solution was adjusted to 1.5 with sulfuric acid. The mixture was then dissolved under heat. Subsequently, the solution was cooled to precipitate 9 g of crystalline DL-valine p-isopropylbenzenesulfonate. The precipitated crystals were recovered by centrifugation, and then dissolved in a large amount of hot water. The solution was passed through an OH-type weakly basic ion-exchange resin to remove p-isopropylbenzenesulfonic acid. The effluent was crystallized through concentration to obtain 3 g of free DL-valine crystals. The analysis of the mother liquor revealed that the precipitation rate of valine was 30% and the purity of the free DL-valine was not less than 99%.

Comparative Example 1

To 20 g of L-valine were added 32.5 g of p-toluenesulfonic acid monohydrate and 47.5 g of water.

The mixture was dissolved at room temperature, and was then cooled to 10° C. A small amount of valine p-toluenesulfonate crystals were precipitated by this procedure. The solubility of L-valine p-toluenesulfonate in water at 10° C. (pH 1.5) was 48% by weight.

Comparative Example 2

To 15 g of L-valine were added 28.5 g of sodium p-n-propylbenzenesulfonate and 56.5 g of water. After the pH was adjusted to 1.5 with sulfuric acid, the mixture was dissolved at 50° C. Then, the solution was cooled to 10° C. to obtain 13 g of L-valine p-n-propylbenzenesulfonate. The analysis of the mother liquor revealed that the precipitation rate of valine was only 30%. The solubility of L-valine p-n-propylbenzenesulfonate in water at 10° C. (pH 1.5) was 29% by weight. The thus-obtained crystals were white fine crystals, the crystal system was a monoclinic system, and the specific gravity of the crystals was 1.27 g/cm$^3$.

Comparative Example 3

Sodium sulfoisophthalate (34.5 g, equimolar amount relative to L-valine) was added to 150 ml of a solution containing 15 g of L-valine, 1.2 g of L-leucine, 1.2 g of L-isoleucine and 1.2 g of L-glutamic acid. After the pH was adjusted to 1.5, the mixture was dissolved under heat. Then, the solution was cooled to precipitate and separate L-valine sulfoisophthalate. The purity of valine in the L-valine sulfoisophthalate crystals was 98%, and the contents of other amino acids were 2%. The yield of valine obtained was 70%. This was dissolved in a large amount of hot water, and the solution was passed through an OH-type weakly basic ion-exchange resin in order to attempt removal of sulfoisophthalic acid and obtain free valine. However, the removal of sulfoisophthalic acid did not proceed fully, and it was difficult to obtain completely free valine by this method. Therefore, the removal of sulfoisophthalic acid was conducted using a strongly acidic ion-exchange resin. However, in this method, the valine crystals precipitated in the eluate and within the resin column when eluting valine from the strongly acidic ion-exchange resin. It was difficult to remove sulfoisophthalic acid at good efficiency.

As mentioned above, when the valine isopropylbenzenesulfonate crystals of the present invention are used to purify valine, valine having a high purity can be produced at low cost by a simple process. This is quite useful industrially. That is, the procedure of the present invention has the effects that since the solubility of the valine p-isopropylbenzenesulfonate is low, valine can be obtained at high efficiency, and valine can be separated at a high rate from amino acids such as leucine and isoleucine, which are usually difficult to separate from valine, because of the specificity of valine p-isopropylbenzenesulfonate. Further, isopropylbenzenesulfonic acid can be easily produced industrially by sulfonating inexpensive isopropylbenzene. Accordingly, the present invention can be easily applied industrially at low cost. It is also easy to separate and obtain valine from valine p-isopropylbenzenesulfonate and to recover p-isopropylbenzenesulfonic acid for reuse.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A crystalline valine p-isopropylbenzenesulfonate comprising a reaction product of equimolar amounts of valine and p-isopropylbenzenesulfonic acid.

2. A process for purifying valine, comprising:

contacting a valine-containing aqueous solution with p-isopropylbenzenesulfonic acid or a water-soluble salt thereof to form crystalline valine p-isopropylbenzenesulfonate in an aqueous medium;

separating the crystalline valine p-isopropylbenzenesulfonate from the aqueous medium; and dissociating the valine p-isopropylbenzenesulfonate to obtain valine.

3. The process of claim 2, wherein the water-soluble salt of p-isopropylbenzenesulfonic acid is an alkali metal salt.

4. The process of claim 2, wherein said dissociating step is performed by adding sufficient hot water to dissolve said crystalline valine p-isopropylbenzene sulfonate and passing the resulting solution through a mildly basic ion-exchange column, thereby adhering p-isopropylbenzene sulfonic acid to said column and allowing valine to pass through said column as effluent.

5. The process of claim 2, wherein said dissociating step is performed by preparing a suspension of said crystalline p-isopropylbenzene sulfonate in water and adding sufficient alkali hydroxide to adjust pH of the suspension to between 5 and 8 to dissociate said crystalline p-isopropylbenzene sulfonate and cause dissolution of p-isopropylbenzene sulfonic acid and precipitation of free valine.

6. The process of claim 5, wherein said pH is adjusted to be between 6 and 7.

7. The process of claim 2, wherein said contacting step is performed by adding said p-isopropylbenzene sulfonic acid or a water-soluble salt thereof to said valine-containing aqueous solution, wherein said valine-containing aqueous solution contains at least 3 g/dl of valine, and adjusting pH of the resulting solution to be between 0.1 and 2.3.

8. The process of claim 7, wherein said adjusting of the pH is performed using an inorganic acid.

9. The process of claim 8, wherein said inorganic acid is selected from hydrochloric acid or sulfuric acid.

10. The process of claim 7, wherein said pH is adjusted to be between 1.0 and 1.7.

11. The process of claim 10, wherein said pH is adjusted to be 1.5.

12. The process of claim 2, wherein said separating step is performed by filtration.

13. The process of claim 2, wherein said separating step is performed by centrifugation.

14. The process of claim 2, wherein after said dissociating step, said valine is isolated and p-isopropylbenzene sulfonic acid is regenerated and recycled back into said contacting step.

15. The process of claim 2, wherein said valine is selected from the group consisting of L-valine, D-valine, DL-valine and mixtures thereof.

16. The process of claim 2, wherein said valine-containing aqueous solution is obtained from hydrolysis of a protein.

17. The process of claim 2, wherein said valine-containing aqueous solution is obtained from fermentation of a microorganism that produces valine.

18. The process of claim 2, wherein said valine-containing aqueous solution is obtained by fermenting a microorganism that produces and accumulates valine and removing cells of said microorganism from said solution.

19. The process of claim 2, wherein said valine-containing aqueous solution is an aqueous solution of DL-valine obtained synthetically by a method producing hydantoin derivatives as contaminants in said aqueous solution.

20. The process of claim 2, wherein in said contacting step p-isopropylbenzenesulfonic acid or a water-soluble salt thereof is added in an amount of from 1.0 to 1.1 mols per mol of valine in said valine-containing aqueous solution.

* * * * *